US012805936B2

(12) United States Patent
Kee et al.

(10) Patent No.: US 12,805,936 B2
(45) Date of Patent: Nov. 24, 2026

(54) METHOD AND SYSTEM FOR DETERMINING A TRAJECTORY OF AN ELONGATED TOOL

(71) Applicant: Biobot Surgical Pte Ltd, Singapore (SG)

(72) Inventors: Yew Hwee Hwee Kee, Singapore (SG); Jia Yun Hwee Hee, Singapore (SG); Lan Eng Hwee Poh, Singapore (SG); Guoyu Qian, Singapore (SG)

(73) Assignee: Biobot Surgical Pte Ltd, Singapore (SG)

(*) Notice: Subject to any disclaimer, the term of this patent is extended or adjusted under 35 U.S.C. 154(b) by 6 days.

(21) Appl. No.: 18/293,310

(22) PCT Filed: Aug. 23, 2022

(86) PCT No.: PCT/SG2022/050600

§ 371 (c)(1),
(2) Date: Jan. 29, 2024

(87) PCT Pub. No.: WO2023/027637

PCT Pub. Date: Mar. 2, 2023

(65) Prior Publication Data

US 2024/0335235 A1 Oct. 10, 2024

(30) Foreign Application Priority Data

Aug. 23, 2021 (SG) .......................... 10202109183Q

(51) Int. Cl.
*A61B 34/10* (2016.01)
*A61B 17/34* (2006.01)

(52) U.S. Cl.
CPC .......... *A61B 34/10* (2016.02); *A61B 17/3403* (2013.01); *A61B 2034/107* (2016.02)

(58) Field of Classification Search
CPC ................ A61B 34/10; A61B 17/3403; A61B 2017/3413; A61B 2034/107;
(Continued)

(56) References Cited

U.S. PATENT DOCUMENTS

2012/0143055 A1 6/2012 Ng et al.
2013/0116548 A1* 5/2013 Kumar .................... A61B 8/12 600/424

(Continued)

FOREIGN PATENT DOCUMENTS

WO 2012082418 A1 6/2012
WO 2016135595 A1 9/2016

(Continued)

OTHER PUBLICATIONS

International Search Report issued in Application No. PCT/SG2022/050600, mailed on Mar. 15, 2023 (4 pages).

(Continued)

*Primary Examiner* — Dianne Dornbusch
(74) *Attorney, Agent, or Firm* — Osha Bergman Watanabe & Burton LLP

(57) ABSTRACT

A method for determining a trajectory of an elongated tool includes receiving positional information of a region of interest and receiving positional information of one or more structures at least partially occluding or obstructing access to the region of interest. Based on positional information of an initial target point in the region of interest, a sagittal plane passing through an imaging device and the initial target point is determined. Based on positional information of an entry point of the elongated tool, a trajectory of the elongated tool substantially along the sagittal plane for advancing the elongated tool to strike the initial target point without striking the one or more structures is determined.

18 Claims, 9 Drawing Sheets

(58) Field of Classification Search
CPC .... A61B 2034/2063; A61B 2034/2065; A61B 8/0841; A61B 8/4245; A61B 34/20; A61B 2034/101; A61B 2034/102
See application file for complete search history.

(56) References Cited

U.S. PATENT DOCUMENTS

| | | | | |
|---|---|---|---|---|
| 2016/0022309 | A1 | 1/2016 | Allaway | |
| 2017/0020558 | A1 | 1/2017 | Xu et al. | |
| 2019/0209130 | A1 * | 7/2019 | Lieblich | A61B 8/12 |
| 2019/0254749 | A1 | 8/2019 | Shochat | |
| 2019/0307515 | A1 | 10/2019 | Naito et al. | |
| 2021/0212767 | A1 * | 7/2021 | Wapler | A61B 34/10 |

FOREIGN PATENT DOCUMENTS

| | | | |
|---|---|---|---|
| WO | 2021105992 | A1 | 6/2021 |
| WO | 2021111445 | A1 | 6/2021 |

OTHER PUBLICATIONS

Written Opinion issued in Application No. PCT/SG2022/050600, mailed on Mar. 15, 2023 (5 pages).
Office Action issued in European Application No. 22 861 807.0-1122, mailed on May 13, 2025 (4 Pages).
Extended European Search Report issued in European Application No. 22861807.0, mailed on Aug. 14, 2025 (10 pages).
Office Action issued in Chinese Application No. 2022800559047 mailed on Jul. 26, 2026 (19 pages).

* cited by examiner

METHOD AND SYSTEM FOR DETERMINING A TRAJECTORY OF AN ELONGATED TOOL

TECHNICAL FIELD

The present invention relates broadly, but not exclusively, to methods and systems for determining a trajectory of an elongated tool.

BACKGROUND

During transperineal prostate procedures where needles are inserted into and around the prostate, a biplane ultrasound probe is normally used to provide real-time imaging. The needles are typically visualized on the sagittal ultrasound view. In order for the needles to be visible on the sagittal ultrasound view, they need to be within the sagittal plane of the ultrasound transducer. A convenient way to achieve this is to have the needles inserted parallel to the axis of the ultrasound probe (see FIG. 1).

Due to conventional visuality restriction, physicians may not always be able to perform operations where the needle is not parallel to the axis of the ultrasound probe as well and as often. This is partly because they may sometimes be constrained by a physical template grid to help with needle placement when operating manually. Even if they were to insert the needles without the template grid, they would have difficulties determining a trajectory that permits visualization in the sagittal view, and would hence mostly insert the needles parallel to the probe axis.

However, there may be scenarios in which it is desirable that the needle is not parallel to the ultrasound probe axis. For example, these may include scenarios that seek to reduce the number of entry points on the perineum, access anterior lesions otherwise obstructed by the pubic arch or any other anatomic structures (needle is angled upwards), access the area between the rectum and the prostate while avoiding the rectal hump (needle is angled downwards), or overcome needle deflection due to prostate tissue density.

In these scenarios, the needles need to be angulated upwards or in other trajectory angles not parallel to the ultrasound probe (see FIG. 2) and it is difficult for the physician to cognitively determine a trajectory for the needle that is still within the sagittal plane. As a result, they may not be able to see the needle clearly in a single sagittal ultrasound view, and may need to rotate the ultrasound probe to see the entire needle trajectory.

Further, when the needle trajectory is not within the sagittal plane, the physician may have to perform multiple rotations of the probe manually, and/or take multiple slices of the transverse view. However, this is cumbersome and time-consuming, and one of the key difficulties of transperineal needle placement.

A need therefore exists to provide a method and system for determining a trajectory of an elongated tool, such as a needle, that can address at least some of the above problems.

SUMMARY

According to an aspect of the present disclosure, there is provided a method for determining a trajectory of an elongated tool, the method comprising:

a) receiving positional information of a region of interest;

b) receiving positional information of one or more structures at least partially occluding or obstructing access to the region of interest;

c) determining, based on positional information of an initial target point in the region of interest, a sagittal plane passing through an imaging device and the initial target point; and d) determining, based on positional information of an entry point of the elongated tool, a trajectory of the elongated tool substantially along the sagittal plane for advancing the elongated tool to strike the initial target point without striking the one or more structures.

Step c) may further comprise automatically determining the positional information of the initial target point based on one or more target point constraints. Alternatively, step c) may further comprise receiving the positional information of the initial target point from a user.

Step d) may further comprise automatically determining the position information of the entry point of the elongated tool based on one or more entry point constraints. The one or more entry point constraints may comprise at least the entry point being on the sagittal plane.

The method may further comprise:

e) receiving updated positional information of either the initial target point or the entry point on the sagittal plane; and f) determining an updated trajectory of the elongated tool substantially along the sagittal plane based on the updated positional information.

Step d) may comprise receiving the positional information of the entry point from a user, and the method may further comprise generating a warning if the trajectory based on said entry point is out of the sagittal plane.

The method may further comprise repeating steps c) and d) for a subsequent target point in the region of interest different from the initial target point if no suitable trajectory exists for the initial target point.

According to another aspect of the present disclosure, there is provided a system for determining a trajectory of an elongated tool, the system comprising a processor;

a computer-readable memory coupled to the processor and having instructions stored thereon that are executable by the processor to:

a) receive positional information of a region of interest;

b) receive positional information of one or more structures at least partially occluding or obstructing access to the region of interest;

c) determine, based on positional information of an initial target point in the region of interest, a sagittal plane passing through an imaging device and the initial target point; and d) determine, based on positional information of an entry point of the elongated tool, a trajectory of the elongated tool substantially along the sagittal plane for advancing the elongated tool to strike the initial target point without striking the one or more structures.

According to another aspect of the present disclosure, there is provided a system comprising:

a processor;

a memory coupled to the processor; and an imaging device coupled to the processor, wherein the memory is configured to receive positional information of a region of interest and positional information of one or more structures at least partially occluding or obstructing access to the region of interest; and wherein the processor is configured to:

determine, based on positional information of an initial target point in the region of interest, a sagittal plane passing through the imaging device and the initial target point; and determine, based on positional information of an entry point of the elongated tool, a trajectory of an elongated tool substantially along the sagittal plane for advancing the elongated tool to strike the initial target point without striking the one or more structures.

The elongated tool may comprise a needle, the system may further comprise a needle guide coupled to the processor, and the needle guide may be configured to align the needle along the determined trajectory.

The system may further comprise an actuator coupled to the processor, and the actuator may be configured to automatically rotate the imaging device based on the determined sagittal plane.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
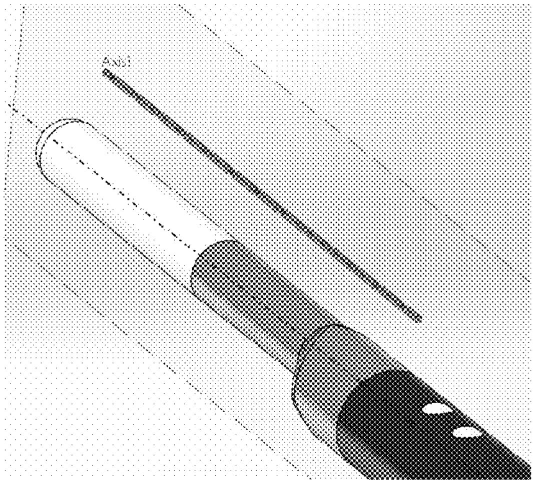
Figure 1 (PRIOR ART)
FIG. 1 shows a schematic diagram illustrating a needle in parallel with an ultrasound probe.
Figure 2:
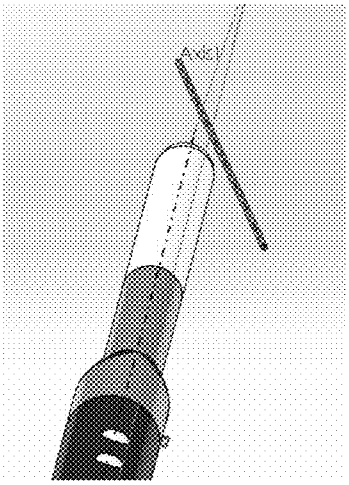
Figure 2 (PRIOR ART)
FIG. 2 shows a schematic diagram illustrating a needle oblique to a plane through an ultrasound probe.
Figure 3:
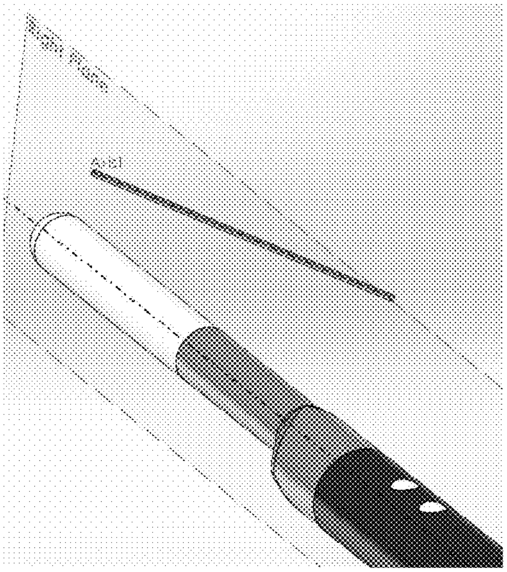
FIG. 3 shows a schematic diagram illustrating a needle positioned at an angle to the ultrasound probe on a plane passing through the ultrasound probe.

The present disclosure provides a method and system for determining a trajectory of an elongated tool. For example, the present method and system can calculate a needle trajectory, taking into consideration multiple factors, such as the entire needle trajectory remains within the sagittal plane and is visible in the sagittal view, the needle tip reaches the target position, critical anatomical structures are avoided, needles are spaced out within the region of interest, needle deflection due to inhomogeneous density of prostate tissue is overcome, or in the case of therapy needles, the ablation volume covers the target volume. The present method also involves rotating the ultrasound probe to a position where the needle is visible in the sagittal view even though the needle may not be parallel with the ultrasound probe, as shown in FIG. 3.

Embodiments will be described, by way of example only, with reference to the drawings. Like reference numerals and characters in the drawings refer to like elements or equivalents.

Figure 4:
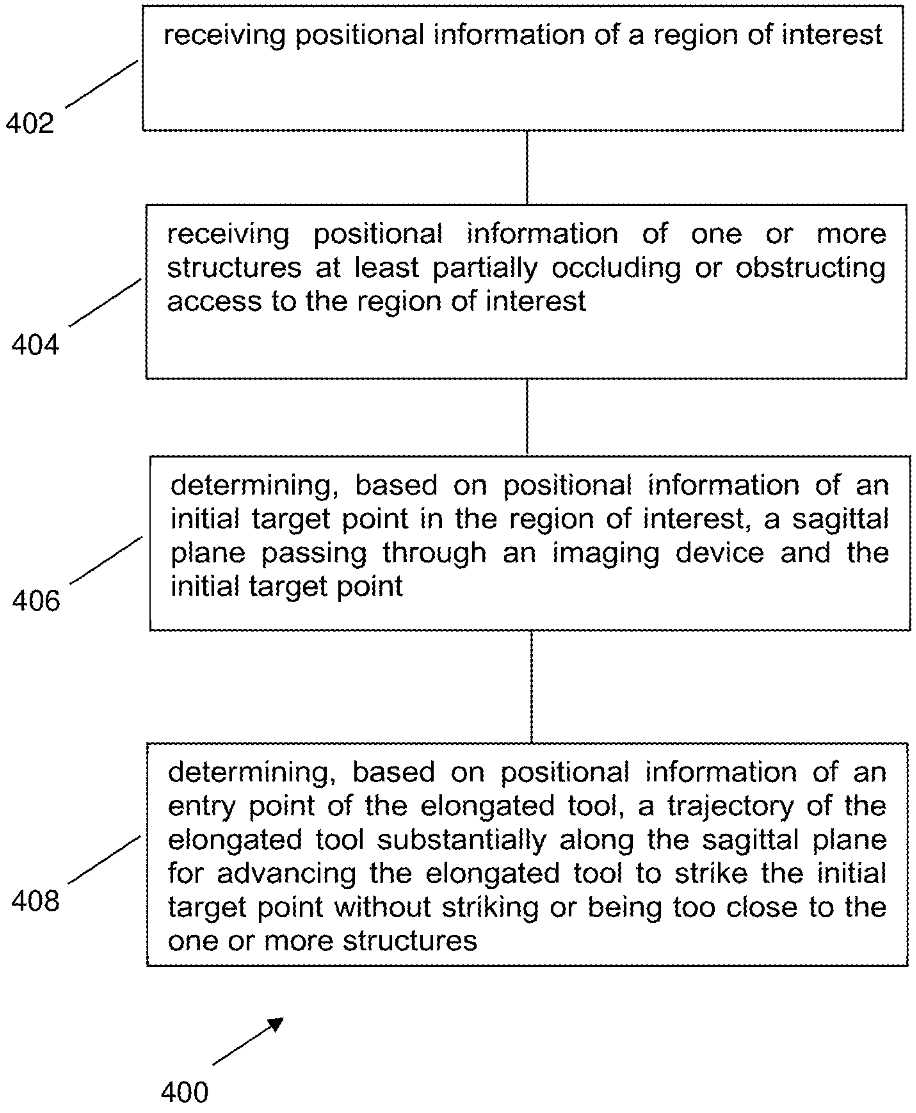
FIG. 4 shows a flow chart illustrating a method for determining a trajectory of an elongated tool according to an example embodiment.

FIG. 4 shows a flow chart 400 illustrating a method for determining a trajectory of an elongated tool according to an example embodiment. At step 402, positional information of a region of interest is received. The region of interest may define an object that is to be accessed by the elongated tool. At step 404, positional information of one or more structures at least partially occluding or obstructing access to the region of interest is received. The positional information of the region of interest and the one or more structures may include sets of coordinates in 3-dimensional (3D) space which can be obtained, for example, by one or more scans followed by the software or user marking these out. At step 406, based on positional information of an initial target point in the region of interest, a sagittal plane passing through an imaging device and the initial target point is determined. The imaging device can be an ultrasound probe for example. At step 406, based on positional information of an entry point of the elongated tool, a trajectory of the elongated tool substantially along the sagittal plane for advancing the elongated tool to strike the initial target point without striking the one or more structures is determined.

In example embodiments, the trajectory of the elongated tool relative to the region of interest and the one or more structures may be displayed on a display device for visualisation. When the initial target point and/or entry point is adjusted, the trajectory of the elongated tool is also adjusted and the display is updated accordingly.

While the examples below are described mainly with reference to trajectory of needles for transperineal procedures, it will be appreciated by a person skilled in the art that the method and system according to the present disclosure can used in other applications for accessing or retrieving occluded objects generally.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as “scanning”, “calculating”, “determining”, “applying”, “extracting”, “generating”, “initializing”, “outputting”, or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a computer or other device selectively activated or reconfigured by a computer program stored in the computer. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a conventional computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the scope of the disclosure.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM, GPRS, 3G, 4G or 5G mobile telephone systems, as well as other wireless systems such as Bluetooth, ZigBee, Wi-Fi. The computer program when loaded and executed on such a computer effectively results in an apparatus that implements the steps of the preferred method.

The present disclosure may also be implemented as hardware elements. More particularly, in the hardware sense, an element is a functional hardware unit designed for use with other components or elements. For example, an element may be implemented using discrete electronic components, or it can form a portion of an entire electronic circuit such as an Application Specific Integrated Circuit (ASIC) or Field Programmable Gate Array (FPGA). Numerous other possibilities exist. Those skilled in the art will appreciate that the system can also be implemented as a combination of hardware and software elements.

According to various embodiments, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which may be described in more detail herein may also be understood as a "circuit" in accordance with an alternative embodiment.

Figure 5:
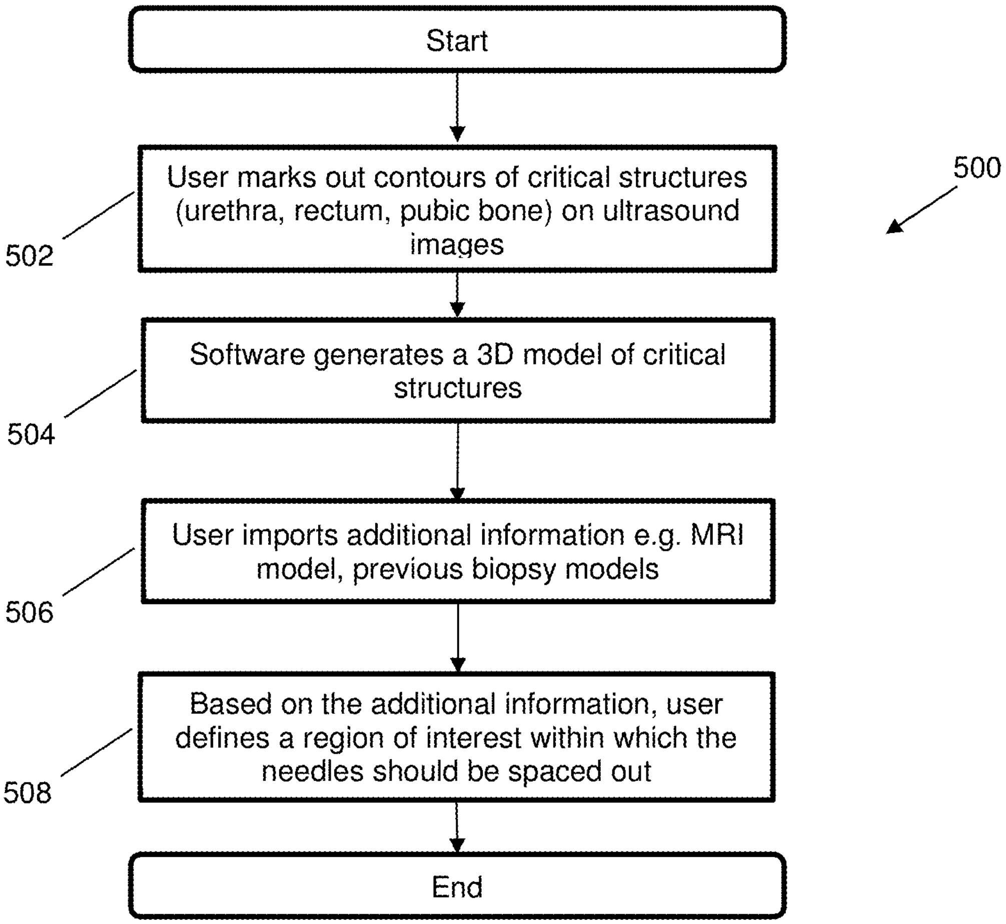
FIG. 5 shows a flow chart illustrating example steps for determining positional information of the region of interest and any structures occluding it.

In example embodiments, positional information of the region of interest and any structures at least partially occluding or obstructing access to it is first determined. The region of interest may be part of an internal organ (e.g. the prostate gland) while the structures occluding it may be other body tissues or parts. FIG. 5 shows a flow chart 500 illustrating example steps for determining positional information of the region of interest and any structures at least partially occluding it. A user, for example, a physician operating a robotic surgical system, may mark out contours of critical structures such as the urethra, rectum, pubic bone etc. on ultrasound images (step 502). Then, the robotic surgical system can generate a 3D model of the critical structures using e.g. built-in software (step 504). The user can import additional information, such as magnetic resonance imaging (MRI) model, previous biopsy models of the same subject/patient, etc. to the robotic surgical system (step 506). Based on the additional information, the user can define the region of interest, e.g. a part or the whole of the prostate gland, that the elongated tool, e.g. a needle, should reach or if there are a few of them, be spaced out within (step 508). It will be appreciated that the positional information of the critical structures and region of interest can be generated directly by the robotic surgical system, or separately by a different computer system and provided to the robotic surgical system in one or more data files.

Figure 6:
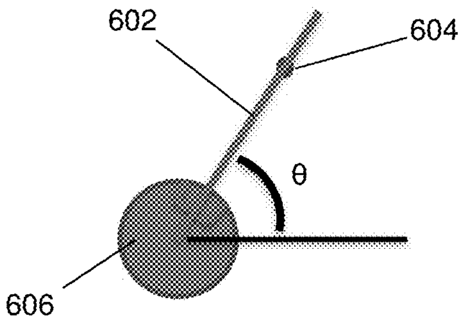
FIG. 6 shows a schematic diagram illustrating a sagittal plane formed between a target point and the ultrasound probe.

After receiving the positional information of the region of interest and any structures at least partially occluding or obstructing access to it, the present method and system can automatically determine and adjust a needle trajectory, which can be used by the robotic surgical system to perform insertion. In one non-limiting implementation, the user can select an initial target point which is disposed in the region of interest. The needle trajectory along the sagittal plane is calculated by first determining an angle of rotation of the sagittal plane passing through the target point and an imaging device, e.g. an ultrasound probe, and then constraining an entry point of the needle within the same sagittal plane by default as the user adjusts the target point. FIG. 6 shows a schematic diagram illustrating an example a sagittal plane 602 formed between a target point 604 and an ultrasound probe 606. In this example, the angle θ between the sagittal plane 602 and a reference line will change as the positional information of the target point 604 is updated, e.g. a different target point is desired.

In this automatic mode, the entry point of the needle can be approximated to the needle guide (NG) point, which is a point along the needle axis that coincides with the distal tip of the physical needle guide. The selection of the entry point may be automatically determined based on one or more entry point constraints, including but not limited to: it lies on the patient's perineum, it is within a selected radius, e.g. 10 mm to 70 mm, from the ultrasound probe centre, it can be up to an angle of ±90° about the midline, it avoids the space around the midline (for example, for a width of 3 mm to 20 mm) where the urethra is, it lies on the sagittal plane, at fixed intervals (which may range from 0.5° to 30°), the user may define the height, or the height may be associated with fixed intervals from the centre of the probe (which may range from 1 mm to 10 mm), a single point per plane or multiple points per plane, and the lowest possible point (i.e. the point closest to the ultrasound probe that is physically accessible by the robotic surgical system and close to the peripheral zone of the prostate) may be chosen.

Figure 7:
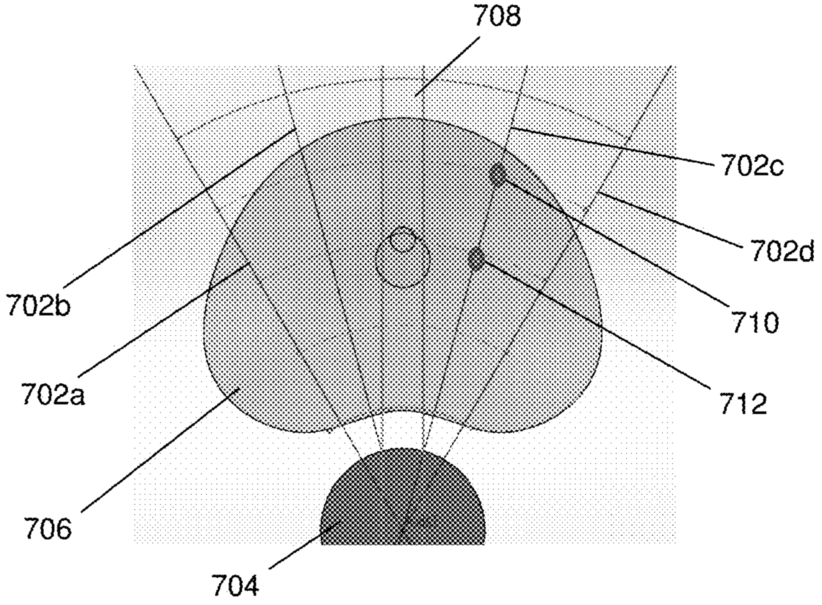
FIG. 7 shows a schematic diagram illustrating automatic selection of the entry point according to an example embodiment.

FIG. 7 shows a schematic diagram illustrating automatic selection of the entry point according to an example embodiment. As can be seen in FIG. 7, multiple planes 702*a*, 702*b*, 702*c*, 702*d* may be formed between the center of the ultrasound probe 704 and the prostate 706 such that the planes 702*a*, 702*b*, 702*c*, 702*d* are each at a respective angle about the midline 708 and hence the midline 708 is avoided. While four planes 702*a*, 702*b*, 702*c*, 702*d* are shown in FIG. 7 as an illustration, it will be appreciated that the number of planes may be greater. If the initial target point is on one of the planes 702*a*, 702*b*, 702*c*, 702*d*, the entry point is constrained to that plane. For example, if target point 710 is on plane 702*c*, entry point 712 is also on plane 702*c* such that, in subsequent procedures, if the needle is inserted at entry point 712, the needle can reach the target point 710 along plane 702*c* without hitting the pre-defined critical structures. In this way, the needle can both perform its intended function while its trajectory can be captured by positioning the sagittal plane of the imaging device with at plane 702*c*.

Figure 8:
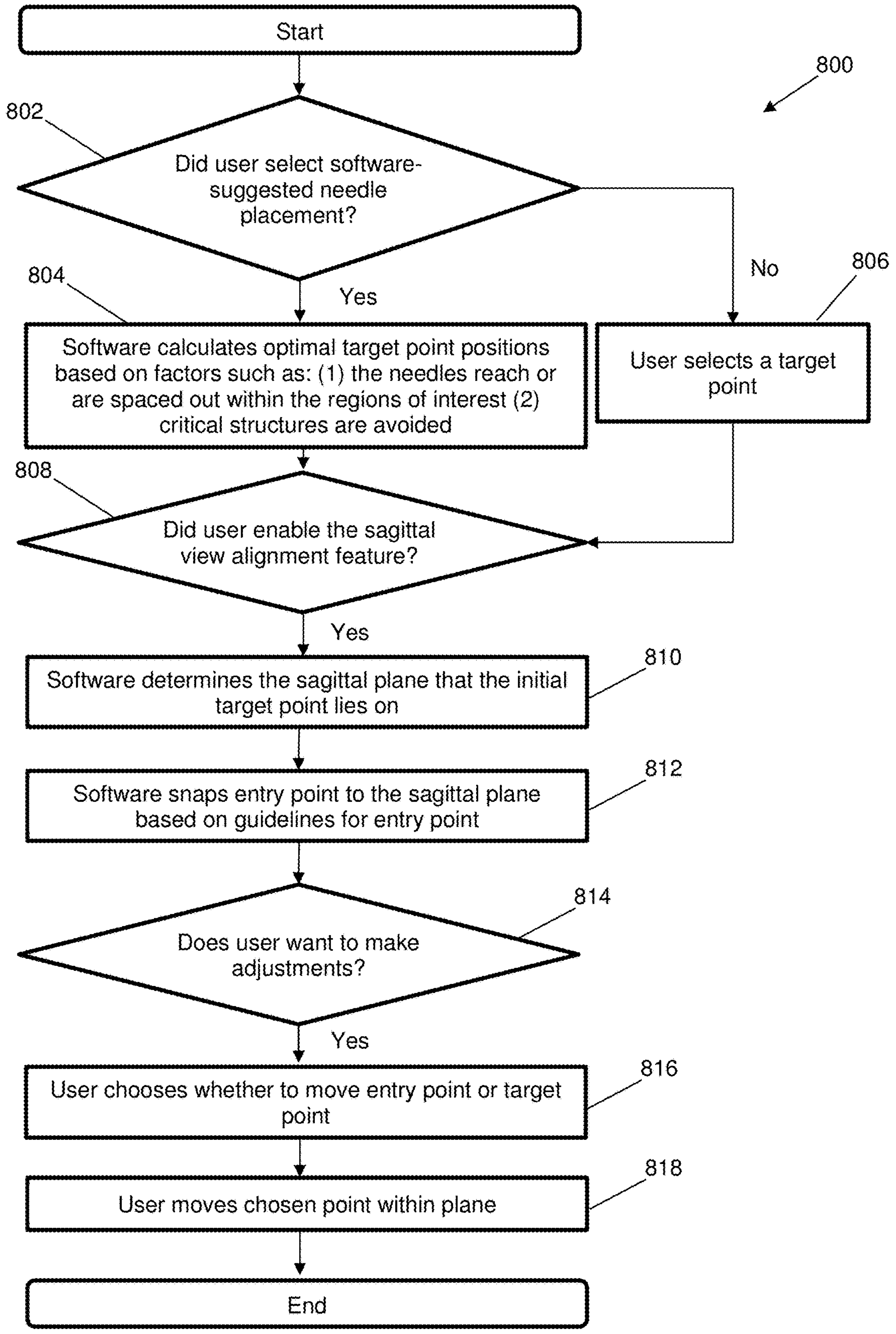
FIG. 8 shows a flow chart illustrating an example implementation of automatic determination of needle trajectory.

FIG. 8 shows a flow chart 800 illustrating an example implementation of automatic determination of needle trajectory. A user interface may prompt whether the user wishes to select the automatic mode (step 802). If the answer is Yes, i.e. the user selects the automatic mode, at step 804, positional information of an initial target point is determined based on pre-programmed algorithms based on one or more target point constrains. In other words, the initial target point is automatically determined by the system. Examples of such target points constraints include, but are not limited to (1) the needles reach or are spaced out within the regions of interest, and (2) critical structures are avoided. For example, to avoid the critical structures, the target points can be such that they are not too close to the critical structures. In the case of the therapy needles, the ablation volume should not cover any part of the critical structures. In some embodiments, the pre-programmed algorithms may make use of artificial intelligence and parameters, such as size and position of the region of interest, needle density, minimum spacing between needles, and size and position of the ablation zone in the case of therapy needles to determine the initial target point. It is possible that to complete the treatment, multiple needles may be used, and each needle has an associated initial target point.

On the other hand, if the answer is No (i.e. the user does not wish to have the target point determined by the system), the user can proceed to select the initial target point at step 806, for example, based on prior experience and/or training.

In either case, the positional information of the initial target point is received and provided to the robotic surgical system. Next, the user interface may display a prompt whether the needle trajectory should be aligned with the sagittal view at step 808. Based on a positive selection (i.e. "Yes" answer by the user), at step 810, the software implementing the present method can determine the sagittal plane that the target point lies on, as discussed above with reference to FIG. 6. Next, at step 812, the software automatically determines the entry point which lies on the sagittal plane determined at step 810, for example, based on one or more entry point constraints as discussed above with reference to FIG. 7. In instances where multiple needles are used, each needle may have a respective entry point and an additional possible constraint on the entry points for the multiple needles is that the multiple needles are all parallel to one another.

After determining the target point and entry point, the recommended trajectory of the needle can be determined and, in some implementations, shown on a display device for visualisation. Such trajectory is generally limited to the sagittal plane determined at step 810, thereby allowing the needle to be imaged by the imaging device during the subsequent procedures. Further, the present method and system provides the flexibility for the user to make adjustments, if desired. For example, at step 814, the user interfaces checks whether the user wishes to make any adjustments. The user, based on prior experience or training, or based on the trajectory provided for visualisation, may decide to adjust either the entry point or the target point at step 816 if the user believes such adjustment may provide a better outcome. After the selection, at step 818, the user moves the chosen point to a more preferred position within the same sagittal plane and the trajectory is automatically updated accordingly based on the same sagittal plane.

It will be appreciated that, in some instances, the initial target point determined by the system or selected by the user may return no suitable needle trajectory. If that happens, another target point is obtained and steps 810 to 812 may be repeated to determine a suitable needle trajectory.

Figure 9:
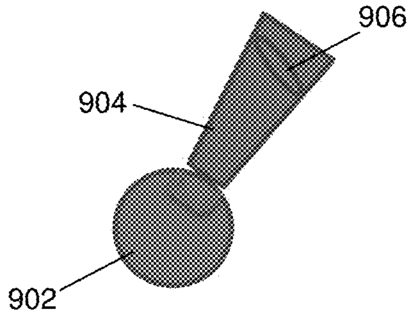
FIG. 9 shows a schematic diagram illustrating possible adjustment of the needle trajectory within boundaries of the sagittal field of view.

In alternate embodiments, instead of automatically planning the needle trajectory as discussed above, the user may manually adjust the planned needle trajectory. The software can rely on predetermined rules to determine whether the needle will remain within the sagittal view after the adjustment. For example, as shown in FIG. 9, the ultrasound probe 902 may have a sagittal field of view 904 that covers a range of angles relative to the reference line, rather than a planar field of view. The software may allow the adjustment if the boundaries of the needle 906 do not go beyond the sagittal field of view 904. If the user plans trajectories that are out of the sagittal field of view 904, the software can provide a warning message. The user can choose to respond to the warning message and adjust the planned needle trajectory until it falls within the sagittal field of view 904. In other words, the present method can balance between providing flexibility for manual adjustment by the user if desired while ensuring the needle can be imaged by the ultrasound probe in subsequent procedures.

In other words, multiple options are available. In the full automatic mode (via step 806 in FIG. 8), the calculation of planned needle trajectory including both the target point and entry point is performed by the software, based on simultaneous consideration of whether all the following factors are fulfilled: (1) the entire needle trajectory remains within the sagittal plane and is visible in the sagittal view, (2) the needles cover the regions of interest, and (3) avoidance of critical anatomical structures. In the semi-automatic mode (via step 804 in FIG. 8), the user can select the target point while the system calculates the entry point. In the manual mode, the user can plan the needle trajectory, but the system can assist with ensuring that the trajectory is within the sagittal field of view.

As described, the present method and system can determine a needle trajectory to be followed. During the needle placement stage, a robotic positioning device of the robotic surgical system guides the insertion of the needle at the pre-defined trajectory. The user is able to see the entire needle trajectory in the sagittal view. There is no need to rotate the ultrasound probe or view the needle at multiple transverse views. This can improve the ease of use. In the event of needle deflection due to tissue inhomogeneity, the robotic system can move the needle guide so that the needle can be inserted to the correct position.

Figure 10:
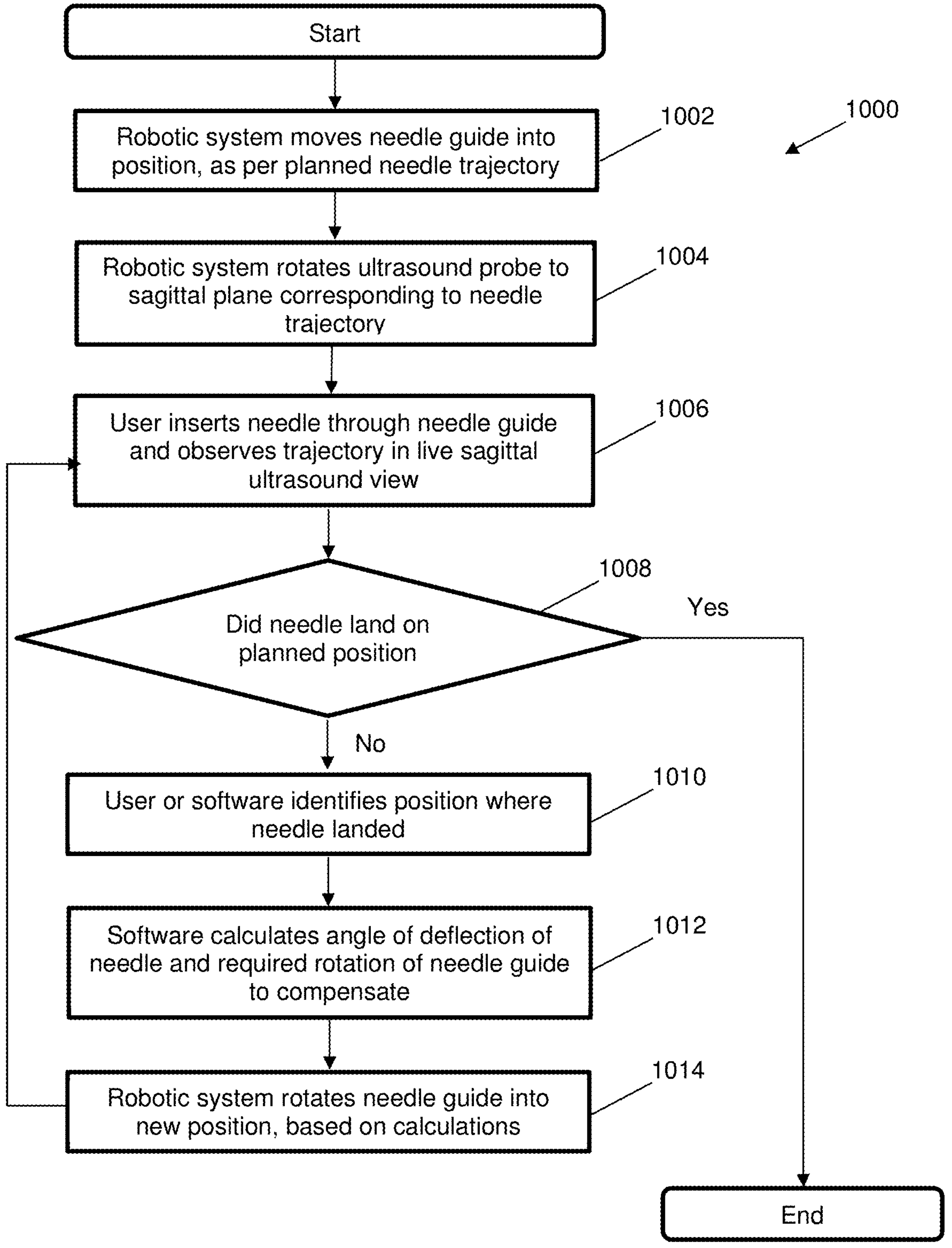
FIG. 10 shows a flow chart illustrating example steps during the needle placement stage according to an implementation.

FIG. 10 shows a flow chart 1000 illustrating example steps during the needle placement stage according to an implementation. At step 1002, the robotic surgical system moves the needle guide into position, as per the planned needle trajectory determined using the steps as described above. For example, the robotic surgical system can move the needle guide such that the NG point is at the entry point and oriented correctly. At step 1004, the robotic surgical system rotates the ultrasound probe to the sagittal plane corresponding to the needle trajectory. The user can then initiate needle insertion through the needle guide and observe the needle in live sagittal ultrasound view, i.e. a real-time display, at step 1006. If it is determined at 1008 that the needle lands on the planned position, i.e. the needle strikes the target point, the placement stage is completed. On the other hand, if the needle does not strike the target point, for example, because of tissue inhomogeneity, at step 1010, the position where the needle lands is identified and provided to the system. The software can then calculate the angle of deflection of needle and required rotation of needle guide to compensate at step 1012. Based on the calculations, at step 1014, the robotic surgical system moves the needle guide into a new position and steps 1006 onward are repeated.

Figure 11:
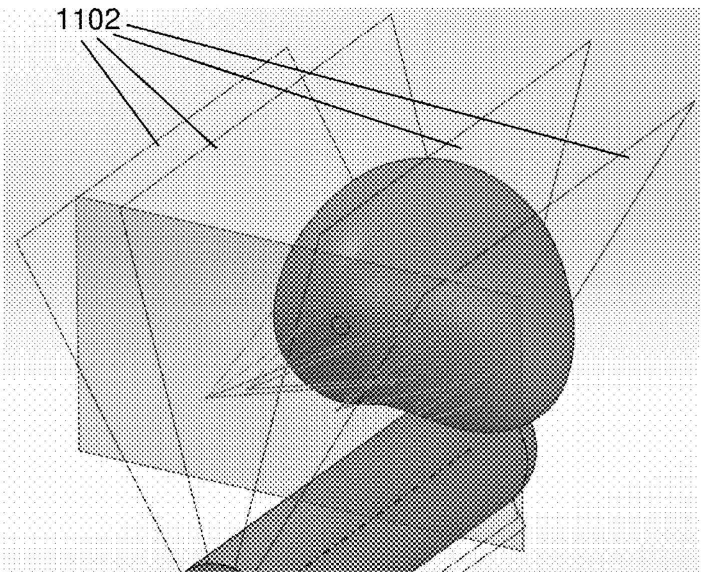
FIG. 11 shows a schematic diagram of sagittal planes and associated needle trajectories with a single entry point per plane and target points spaced out within the prostate.
Figure 12:
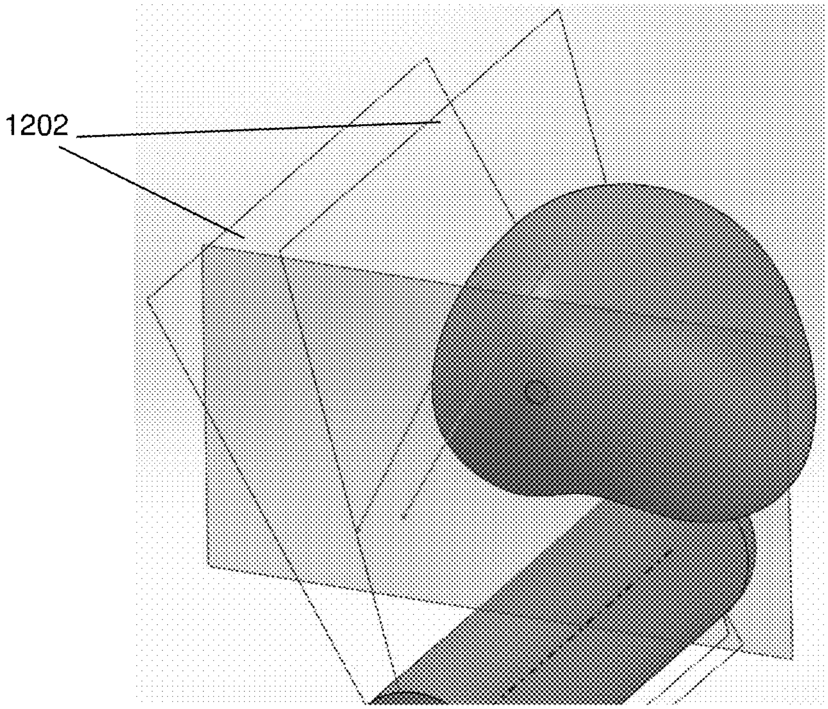
FIG. 12 show a schematic diagram of a reduced number of sagittal planes and associated needle trajectories almost parallel to one another and angulated upwards.

FIGS. 11 and 12 provide possible resultant configurations with the needle trajectories shown in straight lines. FIGS. 11 and 12 demonstrate needle configurations that are made possible by angulation within a sagittal plane, that would be otherwise very difficult with conventional methods. The planes 1102, 1202 represent sagittal planes which the needle trajectories lie on. FIG. 11 shows a configuration where needles are evenly spaced within the prostate, with minimal entry points on the perineum. This is relevant, for example, in a prostate biopsy procedure. In FIG. 11, there are only four entry points on the perineum, with needle trajectories branching out from them. FIG. 12 shows a configuration where the needles are almost parallel to each other but angulated upwards. This is relevant, for example, in a therapy procedure where the therapy requires that the needles are approximately parallel to one another. In FIG. 12, there are two needle trajectories on two sagittal planes, angled upwards but still parallel to one another.

Figure 13:
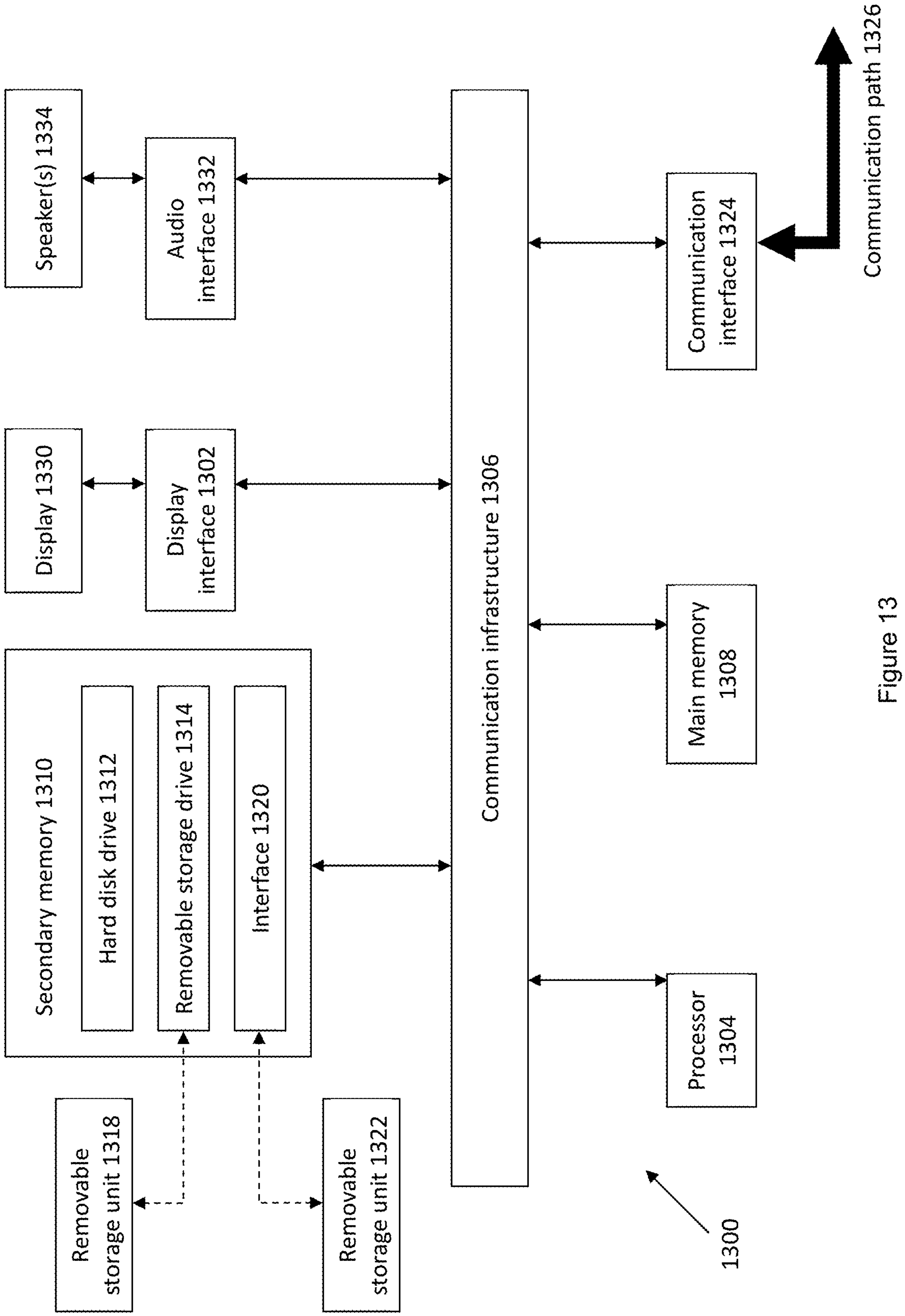
FIG. 13 shows a schematic diagram of a computing device for implementing aspects of the present disclosure.

FIG. 13 depicts an exemplary computing device 1300, hereinafter interchangeably referred to as a computer system 1300, where one or more such computing devices 1300 may be used for determining the trajectory of the elongated tool or implementing the robotic surgical system. The following description of the computing device 1300 is provided by way of example only and is not intended to be limiting.

As shown in FIG. 13, the example computing device 1300 includes a processor 1304 for executing software routines. Although a single processor is shown for the sake of clarity, the computing device 1300 may also include a multi-processor system. The processor 1304 is connected to a communication infrastructure 1306 for communication with other components of the computing device 1300. The communication infrastructure 1306 may include, for example, a communications bus, cross-bar, or network.

The computing device 1300 further includes a main memory 1308, such as a random access memory (RAM), and a secondary memory 1310. The secondary memory 1310 may include, for example, a hard disk drive 1312 and/or a removable storage drive 1314, which may include a floppy disk drive, a magnetic tape drive, an optical disk drive, or the like. The removable storage drive 1314 reads from and/or writes to a removable storage unit 1318 in a well-known manner. The removable storage unit 1318 may include a floppy disk, magnetic tape, optical disk, or the like, which is read by and written to by removable storage drive 1314. As will be appreciated by persons skilled in the relevant art(s), the removable storage unit 1318 includes a computer readable storage medium having stored therein computer executable program code instructions and/or data.

In an alternative implementation, the secondary memory 1310 may additionally or alternatively include other similar means for allowing computer programs or other instructions to be loaded into the computing device 1300. Such means can include, for example, a removable storage unit 1322 and an interface 1320. Examples of a removable storage unit 1322 and interface 1320 include a program cartridge and cartridge interface (such as that found in video game console devices), a removable memory chip (such as an EPROM or PROM) and associated socket, and other removable storage units 1322 and interfaces 1320 which allow software and data to be transferred from the removable storage unit 1322 to the computer system 1300.

The computing device 1300 also includes at least one communication interface 1324. The communication interface 1324 allows software and data to be transferred between computing device 1300 and external devices via a communication path 1326. In various embodiments of the disclosure, the communication interface 1324 permits data to be transferred between the computing device 1300 and a data communication network, such as a public data or private data communication network. The communication interface 1324 may be used to exchange data between different computing devices 1300 which such computing devices 1300 form part an interconnected computer network. Examples of a communication interface 1324 can include a modem, a network interface (such as an Ethernet card), a communication port, an antenna with associated circuitry and the like. The communication interface 1324 may be wired or may be wireless. Software and data transferred via the communication interface 1324 are in the form of signals which can be electronic, electromagnetic, optical or other signals capable of being received by communication interface 1324. These signals are provided to the communication interface via the communication path 1326.

As shown in FIG. 13, the computing device 1300 further includes a display interface 1302 which performs operations for rendering images to an associated display 1330 and an audio interface 1332 for performing operations for playing audio content via associated speaker(s) 1334.

As used herein, the term "computer program product" may refer, in part, to removable storage unit 1318, removable storage unit 1322, a hard disk installed in hard disk drive 1312, or a carrier wave carrying software over communication path 1326 (wireless link or cable) to communication interface 1324. Computer readable storage media refers to any non-transitory tangible storage medium that provides recorded instructions and/or data to the computing device 1300 for execution and/or processing. Examples of such storage media include floppy disks, magnetic tape, CD-ROM, DVD, Blu-Ray™ Disc, a hard disk drive, a ROM or integrated circuit, USB memory, a magneto-optical disk, or a computer readable card such as a PCMCIA card and the like, whether or not such devices are internal or external of the computing device 1300. Examples of transitory or non-tangible computer readable transmission media that may also participate in the provision of software, application programs, instructions and/or data to the computing device 1300 include radio or infra-red transmission channels as well as a network connection to another computer or networked device, and the Internet or Intranets including e-mail transmissions and information recorded on Websites and the like.

The computer programs (also called computer program code) are stored in main memory 1308 and/or secondary memory 1310. Computer programs can also be received via the communication interface 1324. Such computer programs, when executed, enable the computing device 1300 to perform one or more features of embodiments discussed herein. In various embodiments, the computer programs, when executed, enable the processor 1304 to perform features of the above-described embodiments. Accordingly, such computer programs represent controllers of the computer system 1300.

Software may be stored in a computer program product and loaded into the computing device 1300 using the removable storage drive 1314, the hard disk drive 1312, or the interface 1320. Alternatively, the computer program product may be downloaded to the computer system 1300 over the communications path 1326. The software, when executed by the processor 1304, causes the computing device 1300 to perform functions of embodiments described herein.

It is to be understood that the embodiment of FIG. 13 is presented merely by way of example. Therefore, in some embodiments one or more features of the computing device 1300 may be omitted. Also, in some embodiments, one or more features of the computing device 1300 may be combined together. Additionally, in some embodiments, one or more features of the computing device 1300 may be split into one or more component parts.

It will be appreciated that the elements illustrated in FIG. 13 function to provide means for performing the various functions and operations of the servers as described in the above embodiments.

In an implementation, a server may be generally described as a physical device comprising at least one processor and at least one memory including computer program code. The at least one memory and the computer program code are configured to, with the at least one processor, cause the physical device to perform the requisite operations.

It will be appreciated by a person skilled in the art that numerous variations and/or modifications may be made to the present invention as shown in the specific embodiments without departing from the scope of the invention as broadly described. The present embodiments are, therefore, to be considered in all respects to be illustrative and not restrictive.

The invention claimed is:

1. A method for determining a trajectory of an elongated tool, the method comprising:

a) receiving positional information of a region of interest;

b) receiving positional information of one or more structures at least partially occluding or obstructing access to the region of interest;

c) determining, based on positional information of an initial target point in the region of interest and the positional information of the one or more structures, a sagittal plane passing through an axis of an elongated imaging device and the initial target point without passing through the one or more structures, wherein the elongated imaging device is configured to generate an image of an area along the sagittal plane; and d) determining, based on positional information of an entry point of the elongated tool and the positional information of the initial target point, a trajectory of the elongated tool substantially along the sagittal plane for advancing the elongated tool to strike the initial target point without striking the one or more structures.

2. The method as claimed in claim 1, wherein step c) further comprises automatically determining the positional information of the initial target point based on one or more target point constraints.

3. The method as claimed in claim 1, wherein step c) further comprises receiving the positional information of the initial target point from a user.

4. The method as claimed in claim 1, wherein step d) further comprises automatically determining the position information of the entry point of the elongated tool based on one or more entry point constraints.

5. The method as claimed in claim 4, wherein the one or more entry point constraints comprise at least the entry point being on the sagittal plane.

6. The method as claimed in claim 1, further comprising:

e) receiving updated positional information of either the initial target point or the entry point on the sagittal plane; and f) determining an updated trajectory of the elongated tool substantially along the sagittal plane based on the updated positional information.

7. The method as claimed in claim 6, further comprising displaying the trajectory of the elongated tool in real-time as the elongated tool advances between the entry point and the initial target point, wherein displaying comprises displaying the updated trajectory of the elongated tool.

8. The method as claimed in claim 1, wherein step d) comprises receiving the positional information of the entry point from a user, and wherein the method further comprises generating a warning if the trajectory based on said entry point is out of the sagittal plane.

9. The method as claimed in claim 1, further comprising repeating steps c) and d) for a subsequent target point in the region of interest different from the initial target point if no suitable trajectory exists for the initial target point.

10. The method as claimed in claim 1, further comprising displaying the trajectory of the elongated tool in real-time as the elongated tool advances between the entry point and the initial target point.

11. The method as claimed in claim 1, wherein the elongated imaging device comprises an ultrasound probe.

12. The method as claimed in claim 1, wherein step c) further comprises:

determining a plurality of planes that pass through the imaging device and the region of interest, wherein the plurality of planes each correspond to an imaging plane of the elongated imaging device at different possible orientations of the elongated imaging device; and selecting one of the planes passing through the target point from the plurality of planes.

13. A system for determining a trajectory of an elongated tool, the system comprising:

a processor;

a computer-readable memory coupled to the processor and having instructions stored thereon that are executable by the processor to:

a) receive positional information of a region of interest;

b) receive positional information of one or more structures at least partially occluding or obstructing access to the region of interest;

c) determine, based on positional information of an initial target point in the region of interest and the position information of the one or more structures, a sagittal plane passing through an axis of an elongated imaging device and the initial target point without passing through the one or more structures, wherein the elongated imaging device is configured to generate an image of an area along the sagittal plane; and d) determine, based on positional information of an entry point of the elongated tool and the positional information of the initial target point, a trajectory of the elongated tool substantially along the sagittal plane for advancing the elongated tool to strike the initial target point without striking the one or more structures.

14. A system comprising:

a processor;

a memory coupled to the processor; and an elongated imaging device coupled to the processor, the elongated imaging device configured to generate an image of an area along a sagittal plane passing through an axis of the elongated imaging device, wherein the memory is configured to receive positional information of a region of interest and positional information of one or more structures at least partially occluding or obstructing access to the region of interest; and wherein the processor is configured to:

determine, based on positional information of an initial target point in the region of interest and the positional information the one or more structures, the sagittal plane passing through the axis of the elongated imaging device and the initial target point without passing through the one or more structures; and determine, based on positional information of an entry point of an elongated tool and the positional information of the initial target point, a trajectory of the elongated tool substantially along the sagittal plane for advancing the elongated tool to strike the initial target point without striking the one or more structures.

15. The system as claimed in claim 14, wherein the elongated tool comprises a needle, wherein the system further comprises a needle guide coupled to the processor, and wherein the needle guide is configured to align the needle along the determined trajectory.

16. The system as claimed in claim 14, further comprising an actuator coupled to the processor, wherein the actuator is configured to automatically rotate the elongated imaging device based on the determined sagittal plane.

17. The system as claimed in claim 14, wherein the elongated imaging device comprises an ultrasound probe.

18. The system as claimed in claim 14, wherein the processor is further configured to determine a plurality of planes that pass through the imaging device and the region of interest, wherein the plurality of planes each correspond to an imaging plane of the elongated imaging device at different possible orientations of the imaging device, and wherein the trajectory is determined by selecting one of the planes passing through the target point from the plurality of planes.

* * * * *